US008556001B2

(12) United States Patent
Calleri

(10) Patent No.: US 8,556,001 B2
(45) Date of Patent: Oct. 15, 2013

(54) PROCESS FOR DETERMINING THE PRESENCE AND/OR QUANTITY OF $H_2S$ IN SUBSOIL AND RELATED APPARATUS

(75) Inventor: Antonio Calleri, Milan (IT)

(73) Assignee: Geolog S.r.l., Milan (IT)

( * ) Notice: Subject to any disclaimer, the term of this patent is extended or adjusted under 35 U.S.C. 154(b) by 368 days.

(21) Appl. No.: 12/906,982

(22) Filed: Oct. 18, 2010

(65) Prior Publication Data
US 2011/0088947 A1    Apr. 21, 2011

(51) Int. Cl.
*E21B 49/00*    (2006.01)

(52) U.S. Cl.
USPC ......... 175/50; 73/152.18; 73/152.23; 175/58; 175/207; 436/31; 436/32

(58) Field of Classification Search
None
See application file for complete search history.

(56) References Cited

U.S. PATENT DOCUMENTS

| | | | |
|---|---|---|---|
| 2006/0202122 A1* | 9/2006 | Gunn et al. | 250/339.13 |
| 2007/0199872 A1* | 8/2007 | Mueller et al. | 210/189 |
| 2008/0250853 A1* | 10/2008 | Calleri | 73/152.19 |
| 2011/0303463 A1* | 12/2011 | Lessi | 175/50 |

* cited by examiner

*Primary Examiner* — George Suchfield
(74) *Attorney, Agent, or Firm* — John Alumit

(57) ABSTRACT

The present invention relates to a process and related apparatus for determining the presence and/or quantity of $H_2S$ in the drilling debris of a subsoil layer comprising the following working steps: recovering the drilling debris of a layer; degassing the drilling debris from the previous recovery step, and separating a gaseous phase from said debris; clearing the gas released in the step of degassing, and conveying towards an $H_2S$ detector; determining the possible presence and/or quantity of $H_2S$ in the gaseous phase from the steps of degassing and clearing by means of a suitable means of detection; possible repetition of the previous phases at two layers, at least of the subsoil at different levels of depth in relation to the surface, with consequent determination of a distribution profile of $H_2S$ in the subsoil.

10 Claims, 2 Drawing Sheets

PROCESS FOR DETERMINING THE PRESENCE AND/OR QUANTITY OF $H_2S$ IN SUBSOIL AND RELATED APPARATUS

CROSS-REFERENCE TO RELATED APPLICATION

This application claims the benefit of the priority filing date in Italian patent application n° MI2009A001792 filed on Oct. 19, 2009 in the name of GEOLOG S.p.A. The earliest priority date claimed is Oct. 19, 2009.

FEDERALLY SPONSORED RESEARCH

None

SEQUENCE LISTING OR PROGRAM

None

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

The present invention relates to a process for determining the presence and/or quantity of $H_2S$ in subsoil and related apparatus. More particularly, the present invention relates to the determination of the presence and/or quantity of $H_2S$ in subsoil at different depths in relation to the surface and to an apparatus for implementing said process.

The field of the invention is the exploration and exploitation of subsoil resources, more particularly, but not exclusively, oil and geothermal type resources.

In this sector, the established practice of subsoil exploration is by means of drilling wells and the subsequent analysis of drilling mud brought to the surface. Drilling mud is a fluid product that functions to support the drilled hole, and lubricates and cools the auger when the well is drilled. This fluid product also functions to convey drilling debris to the surface, as well as volatile substances released while drilling.

At the surface, drilling debris arrives in a mixture with drilling fluids and possible volatile components dissolved therein. In the field of oil exploration, geological surveillance (mud logging) includes microscope analysis of drilling debris and chemical analysis (mainly of the chromatography type) of gases extracted from drilling mud. These analyses provide useful information both on the nature of the drilled rock layer and on features of oil resources that may exist in the subsoil. The gases present in the subsoil are both of the hydrocarbon and non-hydrocarbon type. Among the gases of the non-hydrocarbon type, hydrogen sulphide ($H_2S$) is of particular importance because of its potential toxicity for humans. When the presence of $H_2S$ is revealed during drilling or its presence in the subsoil presumed, additives (scavengers) are fed into the drilling fluids and into mud whose purpose is that of reacting with gaseous $H_2S$ to form solid compounds to neutralize the potential harmful effects of this gas. On drilling sites, therefore, it is essential to be able to determine the presence of $H_2S$ in the subsoil with precision and as early as possible in order to guarantee maximum safety conditions for workers.

Determination of the quantity of $H_2S$ and its distribution in subsoil is also of fundamental importance for the purpose characterizing the geology of an exploration area to obtain useful information about potential oil resources. With state-of-the-art techniques and instruments, however, it is not possible to obtain sufficiently accurate information about the distribution and quantity of $H_2S$ in subsoil when a well is drilled.

In order to ensure safe working conditions, it is customary to detect the presence of $H_2S$ in the air around the drilling well by means of specific $H_2S$ sensors. The detection of $H_2S$ by sensors is generally reported to the workers by means of light and acoustic alarms. This type of detection can be inadequate from a safety viewpoint because workers are warned only when the risk is present or imminent. This type of detection also cannot be used to estimate the quantity of $H_2S$ effectively present in subsoil. The quantity of $H_2S$ detected in the air, in fact, is strongly influenced by dissolution and disassociation reactions which take place in the subsoil between the $H_2S$ in protonated form and drilling mud. Gaseous $H_2S$ in subsoil reacts with mud generally characterised by a basic pH forming the ionic species $HS^-$ and $S^{2-}$ which remain dissolved in the mud. Moreover, a fraction of $H_2S$ that remains in protonated gaseous form, and detected by sensors when it reaches the surface, is further reduced by the action of scavengers that are deliberately added to neutralise the $H_2S$. The measurement of $H_2S$ in the air around the drilling well, therefore, considerably underestimates the quantity of gaseous $H_2S$ present in subsoil.

For similar reasons, traditional analyses which can be conducted on drilling mud to characterise subsoil also do not give accurate information about the quantity of $H_2S$ present.

The lack of measurement methods capable of determining the quantity of $H_2S$ present in the subsoil with sufficient accuracy makes it extremely difficult to investigate the distribution of this gas when drilling a well. To date, the only systems of direct measurement at depth which allow quantification of gaseous $H_2S$ in subsoil during drilling are those based on the use of special samplers (wireline formation testers) which allow spot sampling of drilled rock formation. These measurement systems, however, interrupt the drilling and entail high costs for the purchase and maintenance of instrumentation for sampling and sample analysis. As such, they have not to date been applied to a significant extent in this sector.

The object of the present invention, therefore, is to provide a process capable of determining the early presence and/or quantity of $H_2S$ in subsoil in order to improve the safety of wording conditions on the drill site.

A second object of the present invention is to provide a process capable of accurately determining the presence and/or quantity of $H_2S$ in subsoil by means of directly detecting gaseous $H_2S$ in drilling debris without interrupting the drilling process.

Moreover, a further object of the present invention is to provide a process capable of determining the $H_2S$ concentration profile in subsoil along the drilling line in order to obtain accurate information about the quantity and distribution of $H_2S$ at depth, and possibly characterise the area of exploration from a geological viewpoint.

SUMMARY

These and other objects of the present invention are achieved by means of a process for determining the presence and/or quantity of H$_2$S in drilling debris of a subsoil layer comprising the following working steps:

a) drilling of a subsoil layer and recovering the drilling debris. Said debris is basically made up of crushed rock and contains variable quantities of gaseous substances present in the drilled subsoil layer which have remained trapped in the form of small bubbles inside rock pores. The gases trapped in the debris, possibly including H$_2$S, can be extracted and separated by subjecting the debris to a process of degassing.

b) Degassing of the drilling debris from step a), and separating a gaseous phase from said debris.

To degas the debris, any device can be used capable of extracting gases trapped in debris and forming a gaseous phase separate therefrom. To obtain a separation of gases from the debris, degassing techniques can be used based on the use of a planetary mill, as well as methodologies based on the cavitation effect induced by the application of acoustic waves, such as high-frequency ultrasounds. Other known technique of mechanical crushing can also be used.

c) Clearing of the gas released in step b) and conveying said gas towards an appropriate H$_2$S detector.

d) Determining the possible presence and/or quantity of H$_2$S in the gaseous phase from steps b) and c) by a suitable means of detection, such as an electrochemical cell sensor or a semiconductor sensor, or any other known state-of-the-art detector.

Alternatively, the concentration of H$_2$S can be determined through any type of chemical analysis suitable for detecting the presence of H$_2$S in the gaseous phase (e.g. chromatographic and/or spectrometric analysis or other known processes). Following step b) of the abovementioned process, separation of a gaseous phase is obtained which comprises not only H$_2$S but also other volatile components possibly present in the drilling debris. It is therefore possible to also convey these gases towards appropriate detectors, to determine their presence and/or quantity, and to determine their concentration profile along a drilling line.

Moreover, the process described above can be integrated in order to determine the H$_2$S distribution profile in subsoil. The determination of said profile along a drilling line requires the measurement of the quantity of H$_2$S in the drilling debris of at least two layers of subsoil, said layers being sampled at different levels of depth in relation to the surface. Said integration of the process is achieved by adding a further step e) to the process described above which consists of repeating steps a) to d) on one or more further layers of subsoil drilling, preferably sampled at regular intervals.

Moreover, the present invention has as a further object, an apparatus for implementing the process described above, comprising:

a container suitable for holding drilling debris and provided with a suitable means for loading and unloading the debris;

means for degassing the drilling debris contained in the container in a watertight environment;

means for clearing gas coming from rock debris and collected inside a crushing container;

means for detecting and/or quantifying the quantity of H$_2$S possibly present in the gaseous phase, said gaseous phase originating from the degassing of the drilling debris.

These and other aspects will be explained in greater detail by the following description of a preferred embodiment of the present invention, to be read by way of an example of the more general principle claimed.

BRIEF DESCRIPTION OF THE DRAWINGS

The following description refers to the accompanying drawings, in which.

DESCRIPTION OF PREFERRED EMBODIMENTS

Figure 1:
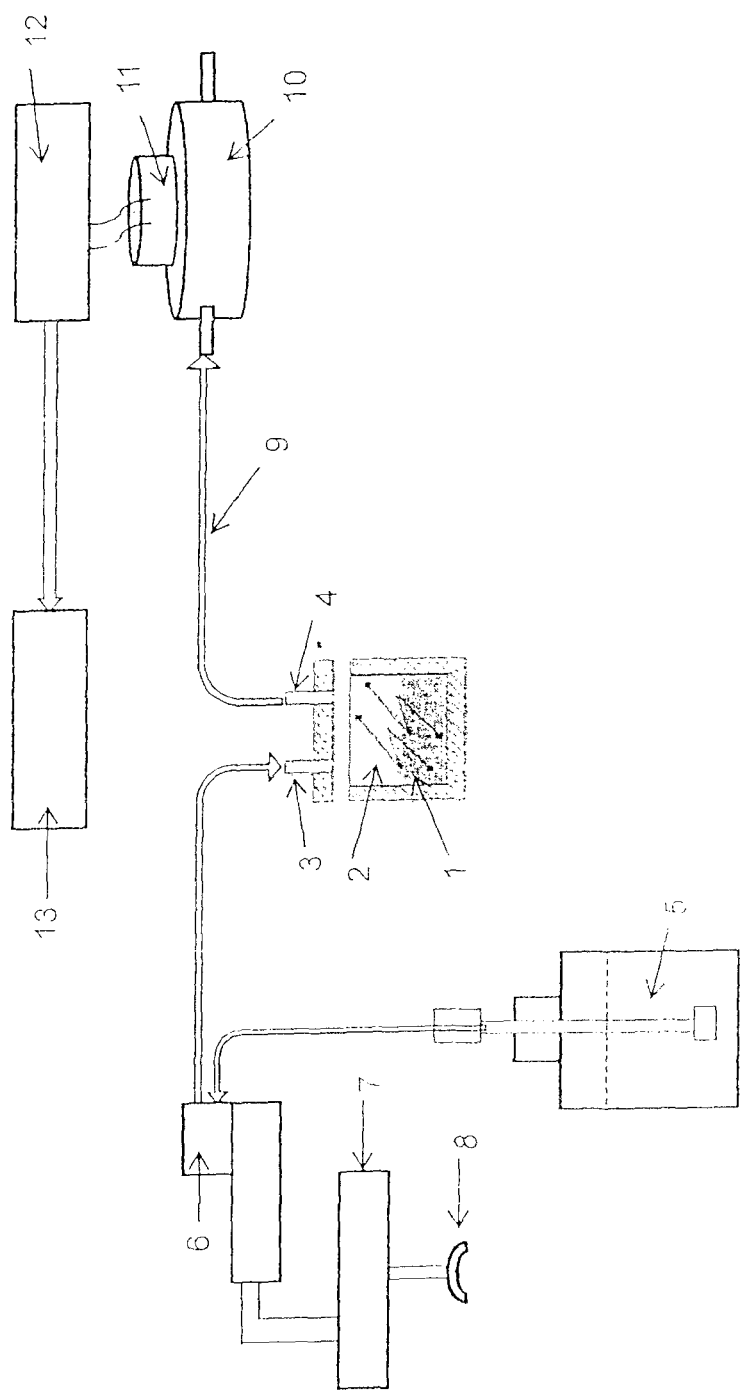
FIG. 1 is a diagram of the process that is the object of the present invention.

Referring to FIG. 1, the process which is the object of the present invention comprises the following working steps:

a) sampling debris from a subsoil layer drilled by an auger and transported to the surface by drilling fluid.

b) degassing the drilling debris from step a) by means of crushing with a planetary mill.

The debris (1) taken from a subsoil layer is placed in a watertight chamber (2) without the need to subject it to any preventive treatment such as washing and/or drying. The cover of the chamber wherein said debris is placed is provided with two valves (3,4); the opening of the first valve (3) allows the entry of water, or another liquid, to clear the gas at the end of the debris crushing phase, while the opening of the second valve (4) releases the gas from a container. The debris is crushed by the action of balls also present in the chamber. More particularly, the jar containing both the sampling debris and the balls is subject to the action of two rotational movements of opposite direction in such a way that the resulting centrifugal forces cause the balls to collide with the sampling debris, crushing them until various gases within them are released. Such gases could include H$_2$S present in originating subsoil layer. During the crushing phase, the two valves (3,4) are kept closed. At the end of the crushing phase, the gaseous phase, which separates from the debris, remains trapped in the same watertight chamber where the crushing takes place.

c) Clearing the gas released in step b) and conveying the gas towards an H$_2$S detector where measurement is to take place.

Clearing of the gas takes place by filling a container wherein the crushed sample is placed with water, or another liquid. The water is aspirated from an external container (5) with a suction pump (6) having a predefined volume and a timed command regulated by a programmable timer (7) and start pushbutton (8) of said timer. Said water is then injected in the jar with constant flow through the entry valve (3) placed on the cover of the jar itself. The cleared gas exits from a second valve (4) and reaches a special container (10) via a gas line (9). Said special container being capable of containing gaseous substances without dispersions.

d) Determining the possible presence and/or quantity of H$_2$S in the gaseous phase from steps b) and c).

Once the gas has arrived at the container (10), the gas is analysed by means of an electrochemical cell sensor with high sensitivity (11) capable of detecting very low concentrations of H$_2$S in the order of parts per billion (ppb). After appropriate amplification and analogue/digital conversion (12), the signal output from the sensor arrives at a computer (13) where appropriate acquisition software is installed. The possible positive response of the sensor as to the presence of H$_2$S in the gaseous phase can also be conveniently used as signal for activating an alarm device; for example, appropriately connecting the sensor to an electronic processor capable of processing a signal transmitted by the same sensor and consequently actuating an alarm device (e.g. of the light and/or acoustic type).

Figure 2:
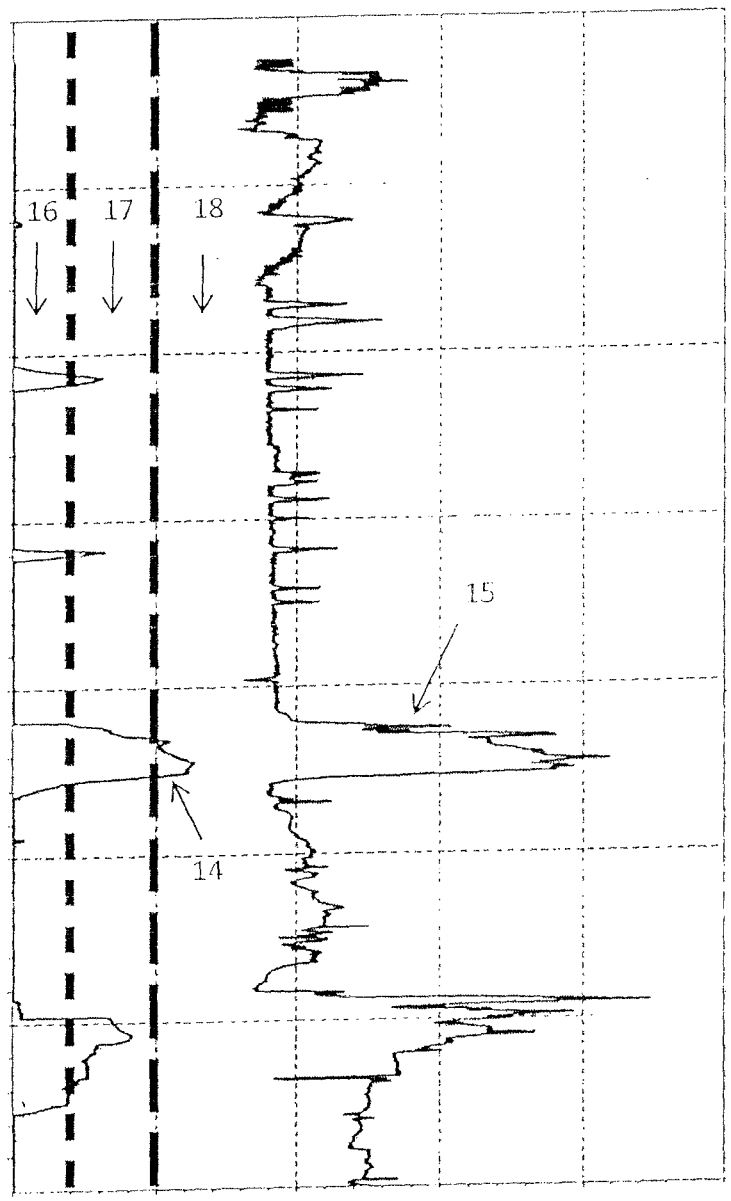
FIG. 2 is a diagram illustrating the distribution profile of H$_2$S in subsoil along a drilling line.

Referring to FIGS. 1 and 2, a second preferred embodiment of the invention consists of a process for determining a distribution profile of $H_2S$ in the subsoil along the drilling line. Said process comprises the determination of the quantity of $H_2S$ in the drilling debris of at least two subsoil layers, said layers being taken at different levels of depth in relation to the surface. Said determination of the concentration profile is performed by repeating the working steps from a) to d), already described, on one or more further subsoil layers drilled, preferably taken at regular intervals. By repeating the quantitative determination of $H_2S$ in the debris from two or more subsoil layers situated at different depths in relation to the surface, it becomes possible to correlate the $H_2S$ concentration with the depth of the subsoil layer along the drilling line of a well. The $H_2S$ distribution profile in subsoil is preferably created by performing a quantitative determination of $H_2S$ on debris from several layers of subsoil taken at a regular distance, one from the other. For example, at a distance variable from one to ten meters, preferably at three metres of distance, one from the other, and in any case, in concordance within the ranges of lithological sampling performed by sector technicians.

By way of example, FIG. 2 shows a diagram of H2S distribution as a function of depth. More particularly, FIG. 2 shows the H2S concentration profile (14) as a function of drilling depth and the total gas concentration profile (15). Represented on the x axis is the concentration of hydrogen sulfide and total gas concentration, and represented on the y axis is the value of drilling depth. Moreover, FIG. 2 shows the range of H2S concentration corresponding to a situation of safety (16), the range of H2S concentration corresponding to a situation of transition (17), and finally the limit of H2S concentration beyond which there is a situation of exploration risk (18).

The advantages offered by the present invention are multiple. A first advantage is the possibility of identifying the early presence of $H_2S$ during subsoil drilling. The abovementioned process, in fact, enables even very small quantities of gaseous $H_2S$ trapped in debris to be detected, allowing for an improvement in safety measures and site working conditions.

A second advantage is the possibility of obtaining quantitative measurements of $H_2S$ present in subsoil that are decidedly more accurate compared to what can be achieved with known state-of-the-art methods. This allows important information to be acquired about the geological nature of subsoil and a determination of the $H_2S$ distribution profiles in subsoil, offering at the same time, an innovative tool for the characterisation of subsoil. The $H_2S$ distribution profiles at depth supply information complementary to those of traditional stratigraphic profiles and contribute to improving the results of so-called "well-to-well correlations," i.e. the correlations of information that can be obtained by drilling a series of wells inside the same geological exploration area. More particularly, the process according to the present invention, allows for a continuous direct measurement with a quantitative $H_2S$ concentration profile at depth.

A third advantage offered by the quantitative determination of trace $H_2S$ present in the subsoil is linked to the possibility of characterising the efficiency of cap rocks at certain levels of depth. These rocks represent impermeable barriers around hydrocarbon tanks, preventing the leakage or migration of oil and/or gas. Finally, greater accuracy of quantitative determinations of $H_2S$ in subsoil also optimizes the use of scavengers as additives to drilling mud to neutralise the presence of $H_2S$, thus avoiding corrosion of well equipment.

Variations of single steps of the process or changes to single elements of the device come within the sphere of protection of the present patent.

What is claimed is:

1. A process for determining the presence and/or quantity of H2S in drilled subsoil layer debris, comprising the following working steps:
    a) drilling a layer of subsoil and recovering of drilling debris of said layer;
    b) degassing the drilling debris from step a) in a watertight environment, and separating a gaseous phase from said debris;
    c) clearing the gas released in step b) and conveying the gas towards an H2S detector;
    d) detecting the possible presence and/or quantity of H2S in the gaseous phase from steps b) and c) by means of said detector; and
    e) determining an H2S distribution profile in the subsoil by repeating the steps a), b), c) and d) on one or more samples from the subsoil layers at different levels of depth in relation to the surface.

2. The process according to claim 1, wherein step b) is performed by subjecting the drilling debris to a process of crushing by means of a planetary mill.

3. The process according to claim 1, wherein step b) is performed by subjecting the drilling debris to a process of crushing by means of a planetary mill.

4. The process according to claim 1, wherein step b) is performed by subjecting the drilling debris to a process of crushing by means of cavitation with high-frequency ultrasounds.

5. The process according to claim 1, wherein step b) is performed by subjecting the drilling debris to a process of crushing by means of cavitation with high-frequency ultrasounds.

6. The process according to claim 1, wherein step b) is performed by subjecting the drilling debris to a process of mechanical crushing inside a watertight container.

7. The process according to claim 1, wherein the means of detecting the possible presence and/or quantity of H2S comprise a specific sensor with high resolution for the detection of H2S.

8. The process according to claim 1, wherein step d) is performed by subjecting the gaseous phase to chromatographic and/or mass spectrometry analysis.

9. The process according to claim 1, wherein the samples from subsoil layers at different levels of depth are each taken equidistant from the next, between 1 m to 10 m.

10. The process according to claim 1, wherein the means of detection of H2S in the gaseous phase are connected to a known alarm device, via an electronic processor which, in the case of a positive signal transmitted by the same sensor, actuates the alarm device.

\* \* \* \* \*